United States Patent [19]

Haynes

[11] Patent Number: 5,207,101
[45] Date of Patent: May 4, 1993

[54] TWO-WIRE ULTRASONIC TRANSMITTER

[75] Inventor: Kevin M. Haynes, Northlake, Ill.

[73] Assignee: Magnetrol International Inc., Downers Grove, Ill.

[21] Appl. No.: 755,813

[22] Filed: Sep. 6, 1991

[51] Int. Cl.$^5$ .............................................. G01N 9/24
[52] U.S. Cl. ................................. 73/597; 73/290 V
[58] Field of Search ................. 73/290 V, 597, 602, 73/620; 340/621; 367/901, 908

[56] References Cited

U.S. PATENT DOCUMENTS

| | | | |
|---|---|---|---|
| 4,221,004 | 9/1980 | Combs et al. | 367/114 |
| 4,229,798 | 10/1980 | Rosie et al. | 364/564 |
| 4,400,976 | 8/1983 | Blades | 73/290 V |
| 4,480,323 | 10/1984 | Page | 367/131 |
| 4,523,472 | 6/1985 | Blades | 73/632 |
| 4,762,001 | 8/1988 | Wuttke | 73/597 |
| 4,785,664 | 11/1988 | Reebs | 340/621 |
| 4,821,215 | 4/1989 | Woodward | 364/550 |
| 4,853,694 | 8/1989 | Tomecek | 73/290 V |
| 4,945,276 | 7/1990 | Mylvaganam et al. | 73/290 V |

OTHER PUBLICATIONS

"A Two-Wire Ultrasonic Level Meter With Piezoelectric Polymer-Film Sensor"-Owada et al., 1988.

*Primary Examiner*—Louis Arana
*Attorney, Agent, or Firm*—Wood, Phillips, VanSanten, Hoffman and Ertel

[57] ABSTRACT

A two-wire ultrasonic transmitter senses level of a material and controls current of power supplied thereto to a magnitude representing sensed level The transmitter comprises a transducer mounted in proximity to a material, the level of which is being sensed. A power supply circuit receives power for operating the instrument. A drive circuit is connected to the transducer and the power supply circuit and periodically energizes the transducer to transmit an energy pulse to be reflected off of a surface of the sensed material. An amplifier circuit is connected to the transducer and develops an analog signal having a magnitude corresponding to reflected energy received by the transducer. A control circuit is operatively coupled to the drive circuit and the amplifier circuit and determines time difference between a first time when the drive circuit energizes the transducer and a second time when the analog signal is above the threshold, the time difference representing level, and energizes the amplifier circuit for a select minimum time duration commencing subsequent to energization of the transducer and terminating after receipt of a return echo pulse A current control circuit is coupled to the control circuit for controlling current received by the power supply circuit to a magnitude representing sensed level.

20 Claims, 10 Drawing Sheets

TWO-WIRE ULTRASONIC TRANSMITTER

FIELD OF THE INVENTION

This invention relates to process control instruments, and more particularly, to a two-wire ultrasonic transmitter.

BACKGROUND OF THE INVENTION

Process control systems require the accurate measurement of process variables. Typically, a primary element senses the value of a process variable and a transmitter develops an output having a value that varies as a function of the process variable. For example, a level transmitter includes a primary element for sensing level and a circuit for developing an electrical signal proportional to sensed level.

An electrical transmitter must be connected to an electrical power source to operate. One form of such a transmitter, known as a four-wire transmitter, includes two terminals for connection to a power source and two terminals for carrying a loop signal proportional to the process variable. This signal can be used as an input to a controller or for purposes of indication. Because the instrument is connected directly to a power source, power consumption is a less critical factor in design and use of the same.

The use of a four-wire transmitter, as discussed above, requires the use of four conductors between the transmitter and related loop control and power components. Where transmitters are remotely located, such a requirement is undesirable owing to the significant cost of cabling. To avoid this problem, instrument manufactures have strived to develop devices known as two-wire, or loop powered, transmitters. A two-wire transmitter includes two terminals connecting to a remote power source, with the transmitter controlling loop current drawn from the power source proportional to the process variable. A typical instrument operates off of a 24 volt DC source and varies the signal current in the loop between four and twenty milliamps DC. Because of these operating requirements the design of the transmitter in terms of power consumption is critical. For example, when a low level signal of four milliamps is transmitted, there is minimal power available to be consumed by the instrument. Therefore, circuits must be designed to operate off of such minimal available power.

One known form of level sensing instruments is an ultrasonic through-air, or sonar, transmitter. Such a transmitter transmits pulses of sound energy through the air above a liquid surface. Since the sound energy is at a frequency above that audible to humans, it is called ultrasound. The pulse of sound energy is provided by a transducer which acts to change electrical energy to mechanical vibration. The pulse of sound travels down from the transducer face to the liquid surface and is reflected back to the transducer. The transducer converts mechanical vibration from the received sound pulse back into an electrical signal. The transmitter circuitry monitors the time of flight from the transmission to the receipt of the sound pulse to determine the fluid distance from the transducer, i.e. level.

A typical transducer, such as a piezoelectric crystal, as well as the receiver and amplification circuits, have high power requirements. This requirement is compounded with a through air transmitter, as opposed to a through liquid transmitter, as air is a vibration insulator, and in process control applications in which greater level spans, such as on the order of thirty feet, are necessary. Thus, ultrasonic transmitters have generally been of the four-wire type.

Further, it is desirable that a level transmitter be operated in hazardous locations in which the transmitter cannot cause the ignition of hazardous gases or liquids. While to some extent this problem can be addressed using explosion-proof housing, it is desirable to use circuits with limited energy storage to prevent spark occurrence.

The present invention is directed to overcoming one or more of the problems set forth above.

SUMMARY OF THE INVENTION

In accordance with the invention, there is disclosed herein a two-wire ultrasonic through air transmitter.

Broadly, there is disclosed herein an instrument for sensing level of a material including a transducer and means for mounting the transducer in proximity to a material, the level of which is being sensed. A drive circuit is connected to the transducer and includes means for periodically energizing the transducer to transmit an energy pulse to be reflected off a surface of the sensed material. An amplifier circuit is connected to the transducer and includes amplifier means for developing an analog signal having a magnitude corresponding to reflected energy received by the transducer. A detector circuit is connected to the amplifier circuit for determining if the analog signal has a level above a select threshold, representing receipt of a return echo pulse. A control circuit is operatively coupled to the drive circuit, the amplifier circuit and the detector circuit and includes level determining means for determining a time difference between a first time when the drive circuit energizes the transducer and a second time when the analog signal is above the threshold, the time difference representing level, and amplifier control means for energizing the amplifier circuit for a select minimum time duration commencing subsequent to energization of the transducer and terminating after receipt of a return echo pulse.

In accordance with one aspect of the invention, the control circuit further comprises detector control means for enabling the detector circuit for a select minimum time duration commencing subsequent to energization of the transducer and terminating after receipt of a return echo pulse.

It is a feature of the invention that the detector control means enables the detector circuit subsequent to the amplifier control means energizing the amplifier circuit.

It is another feature of the invention that the amplifier circuit comprises a power source and a switch controlled by the amplifier control means for selectively controlling coupling of the power source to the amplifier means.

It is another feature of the invention that the amplifier circuit comprises a ring down attenuator circuit operatively coupled to the transducer.

It is a further feature of the invention that the control circuit includes window determining means for selecting the time duration to be a minimum necessary to allow receipt of a return echo pulse.

It is still another feature of the invention that the window determining means selects a start time for the time duration relative to a previously determined time difference.

There is disclosed in accordance with another aspect of the invention a two-wire ultrasonic transmitter for sensing level of a material and controlling current of power supplied thereto to a magnitude representing sensed level. The transmitter comprises a transducer and means for mounting the transducer in proximity to a material, the level of which is being sensed. A power supply circuit receives power for operating the instrument. A drive circuit is connected to the transducer and the power supply circuit and includes means for periodically energizing the transducer to transmit an energy pulse to be reflected off of a surface of the sensed material. An amplifier circuit is connected to the transducer and includes amplifier means for developing an analog signal having a magnitude corresponding to reflected energy received by the transducer. A control circuit is operatively coupled to the drive circuit and the amplifier circuit and includes level determining means for determining a time difference between a first time when the drive circuit energizes the transducer and a second time when the analog signal is above the threshold, the time difference representing level, and amplifier control means for energizing the amplifier circuit for a select minimum time duration commencing subsequent to energization of the transducer and terminating after receipt of a return echo pulse. Current control means are coupled to the level determining means for controlling current received by the power supply circuit to a magnitude representing sensed level.

It is a feature of the invention that the current control means controls current to a range of four to twenty milliamps DC. It is another feature of the invention that the power supply circuit receives a maximum 28 volt DC power at a maximum of 93 milliamps DC to provide an intrinsically safe transmitter.

It is an additional feature of the invention that the control circuit comprises a drive control circuit for operating the drive circuit to transmit a plurality of energy pulses seriatim commencing at said first time.

It is still another feature of the invention that the transmitter comprises means for sensing temperature at the transmitter and wherein the level determining means includes means for compensating sensed level responsive to sensed temperature.

Further features and advantages of the invention will readily be apparent from the specification and from the drawings.

BRIEF DESCRIPTION OF THE DRAWINGS

FIG. 3a+b is a schematic diagram illustrating a circuit on a logic printed circuit board of the transmitter of FIG. 1;

FIG. 4a+b is a schematic diagram illustrating a circuit on an amplifier circuit board of the transmitter of FIG. 1;

DETAILED DESCRIPTION OF THE INVENTION

Figure 1:
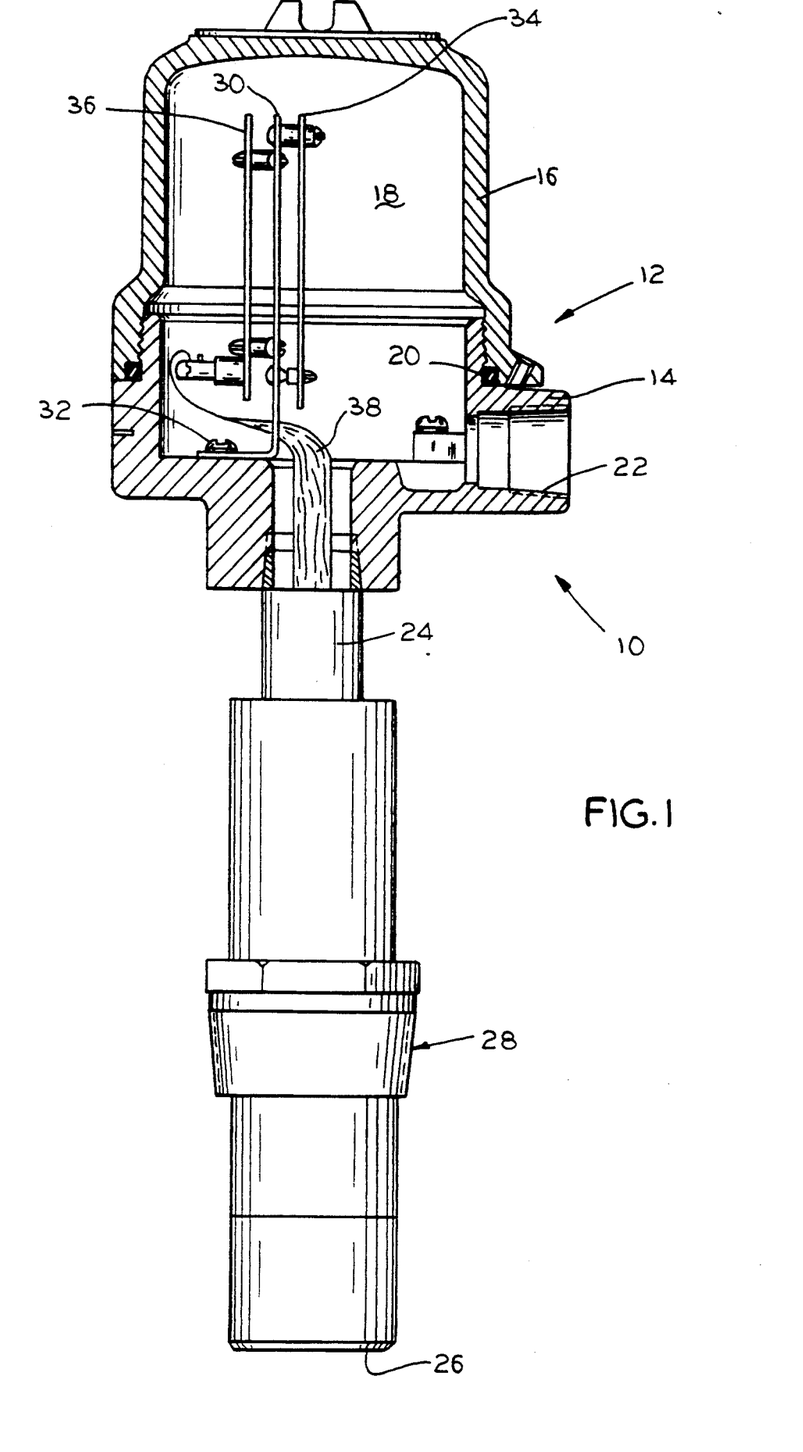
FIG. 1 is an elevational, partial sectional view of the ultrasonic transmitter according to the invention.

With reference to FIG. 1, an ultrasonic through air transmitter 10 according to the invention is illustrated. The transmitter 10, as discussed more specifically below, can be operated in hazardous locations and is of the two-wire type. The transmitter 10 is operable to transmit a sound pulse directed at a surface of a material, the level of which is being sensed, and to receive a reflective sound signal. The time of flight is monitored to determine distance from the transmitter 10 to the surface. Being of the two-wire type, the transmitter 10 receives a user supplied voltage and draws a controlled amount of current based on user set control switches and the distance measured to the surface.

The transmitter 10 comprises a housing 12 including a base 14 threadably receiving a cover 16 to define an interior space 18. An O-ring 20 seals the interior space 18 from the space outside of the enclosure 12. A conduit port 22 is provided for connection to a conduit to connect the transmitter 10 to remote control or indicating equipment. A hollow pipe 24 extends downwardly from the base 14 and is closed at a distal end 26. An NPT-type connector 28 is provided for threadably connecting the pipe 24 to a vessel or tank, having a material the level of which is to be sensed.

Figure 4A:
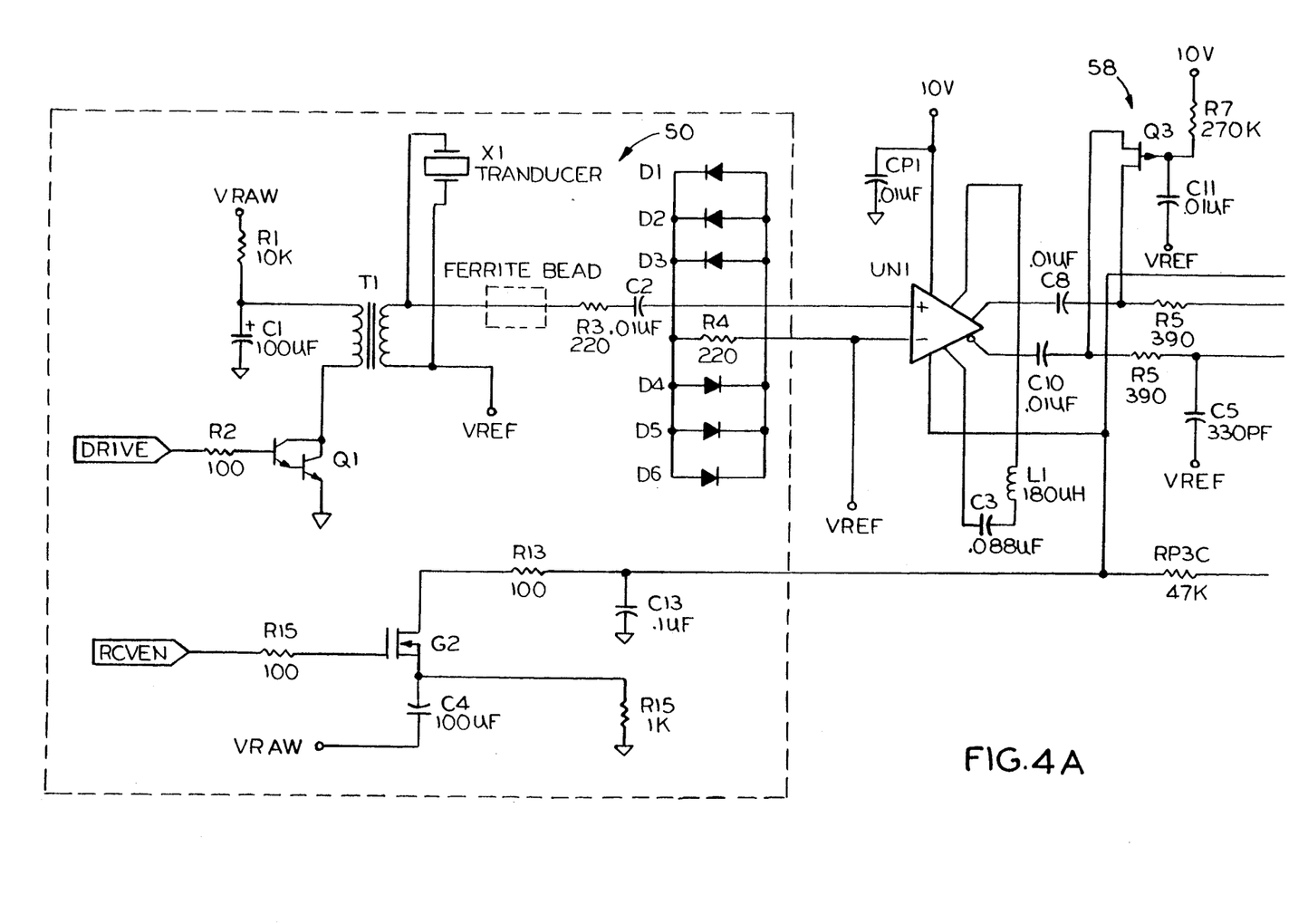
Figure 4B:
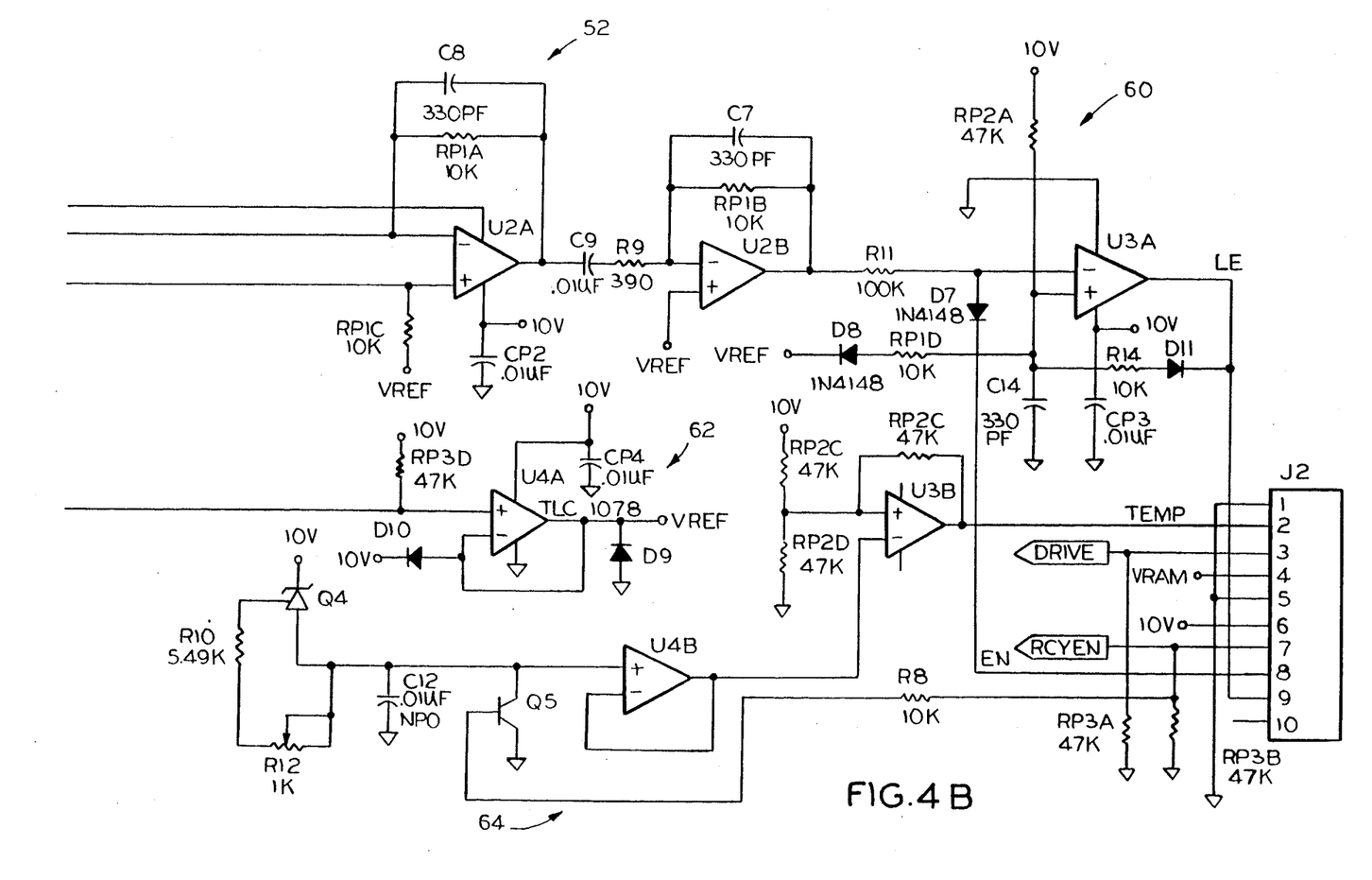

A bracket 30 is mounted to the base 14 using two screws 32 within the space 18. Mounted to the bracket 30 are a power supply printed circuit board 34 and a logic printed circuit board 36. A multiconductor cable 38 extends from the logic printed circuit board and down through the pipe 24 to an amplifier printed circuit board (not shown) including a transducer, discussed relative to the schematic of FIG. 4.

In operation, the transmitter 10 is operable to measure distance from the tube closed end 26 to a liquid surface, representing level of a material in the associated vessel. The transmitter 10 and its associated circuitry converts the sensed distance to control current drawn by the transmitter 10.

The enclosure 12 may be of the explosion-proof type, such as a Nema 7/9 enclosure. Moreover, to be operated in hazardous locations, the transmitter 10 is designed as an intrinsically safe entity when used with an intrinsic safety barrier as rated to limit incoming voltage to 28 volts DC maximum and current to 93 milliamps DC maximum.

Figure 2:
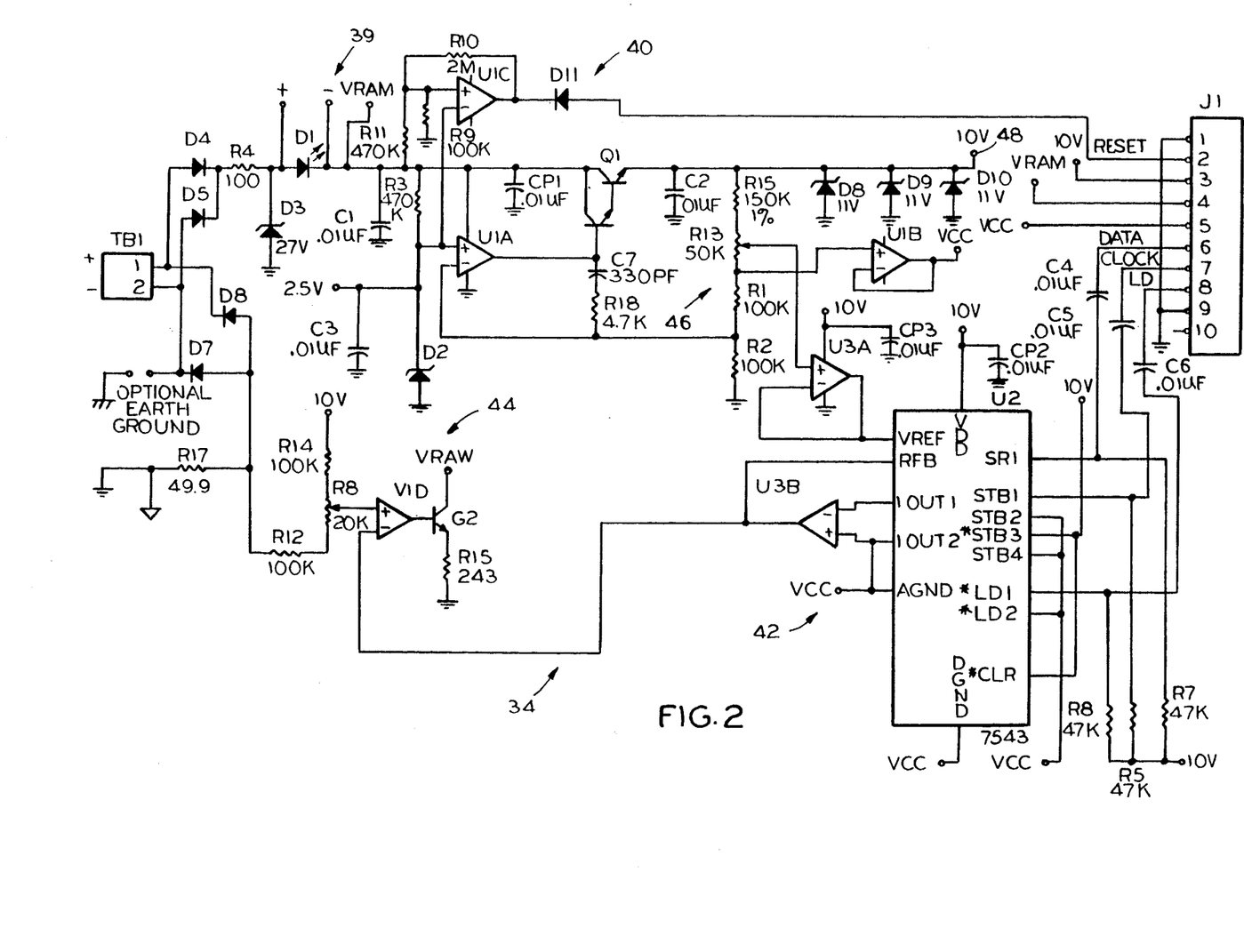
FIG. 2 is an electrical schematic diagram illustrating a circuit on a power supply printed circuit board of the transmitter of FIG. 1.

With reference to FIG. 2, a schematic diagram illustrates a power supply circuit on the power supply printed circuit board 34, see FIG. 1. Included on this board are an input circuit 39, a voltage regulation circuit 40, a digital to analog (D/A) conversion circuit 42, and a current control circuit 44.

The input circuit 39 receives customer supplied voltage and draws a controlled amount of current based on customer set control switches and the distance measured to the liquid surface. A customer connects a 24 volt DC power supply to a terminal strip TB1. A plurality of diodes D4–D7 are provided for polarity protection and to ensure operation regardless of the polarity of connection to the terminal strip TB1. A resistor R4 is connected to the diodes D4 and D5 and also to a diode D3 to limit input current and voltage. An LED diode D1 connected between the junction of the resistor R4 and diode D3 and a Vraw node indicates if power is applied to the circuit. Since current drawn by the transmitter passes through the LED D1, the intensity indicates the current level being drawn and thus level being sensed. The Vraw node provides unregulated power. A diode D2 is connected via a resistor R3 to the Vraw node to provide a precision reference voltage requiring minimal quiescent current. This reference voltage is used by the voltage regulator circuit 40.

The voltage regulator circuit 40 utilizes closed loop control and includes an NPN Darlington transistor Q1 connected to the Vraw node. The transistor Q1 operates as the regulator's emitter follower. The output from the transistor Q1 is connected to a voltage divider circuit 46 consisting of series connected resistors R16, R13, R1 and R2. The junction between the resistors R1 and R2 is connected to the inverted input of an operational amplifier U1A. The non-inverted input is connected to the voltage reference diode D2. The output is connected to the transistor Q1. In this arrangement, the operational amplifier U1A attempts to keep its inputs at the same voltage. Thus, its output is adjusted to obtain the output voltage required to keep its inverted input at 2.5 volts. The output from the transistor Q1 is regulated at a node 48 to ten volts DC. A plurality of diodes D8-D10 are connected to the node 48 for intrinsic safety to assure that the regulated voltage does not exceed 12 volts. Also, filter capacitors C1, C2, CP1 and CP3 are selected to be 0.01 uF owing to the requirements of intrinsic safety that no circuit may store sufficient energy to be able to cause a spark.

An operational amplifier U1B has its non-inverted input connected to the junction of the resistors R13 and R1 and its output connected to its inverted input. The amplifier U1B acts as a follower to provide the regulated voltage VCC which is approximately five volts.

An additional operational amplifier U1C acts as a voltage comparator to monitor incoming raw voltage at the Vraw node via a voltage divider consisting of resistors R9 and R11 and a feedback resistor R10. If the voltage at the Vraw node drops below a threshold, then the output of the amplifier U1C is pulled low causing a *RESET control line to the logic circuit via a connector J1 to be reset. As a result, the logic is always reset prior to loss of the supply voltage, and does not clear reset until the supply voltages are stabilized.

The D/A conversion circuit 42 includes an operational amplifier U3A having a non-inverted input connected to the wiper of the variable resistor R13 and its output connected to its inverted input and to the Vref terminal of a D/A converter U2. The amplifier U3A is a follower to provide the regulated reference voltage to the converter U2. The D/A converter U2 may comprise, for example, a type PM-7543 12-bit serial input multiplying CMOS D/A converter, such as manufactured by Precision Monolithics, Inc. The converter U2 converts serial data input present at the SRI pin into current output at pins Iout1 and Iout2. The rising or falling edges of strobe inputs (STB) are used to clock the serial data into an input shift register transferred to a converter register using load inputs.

Figure 3A:
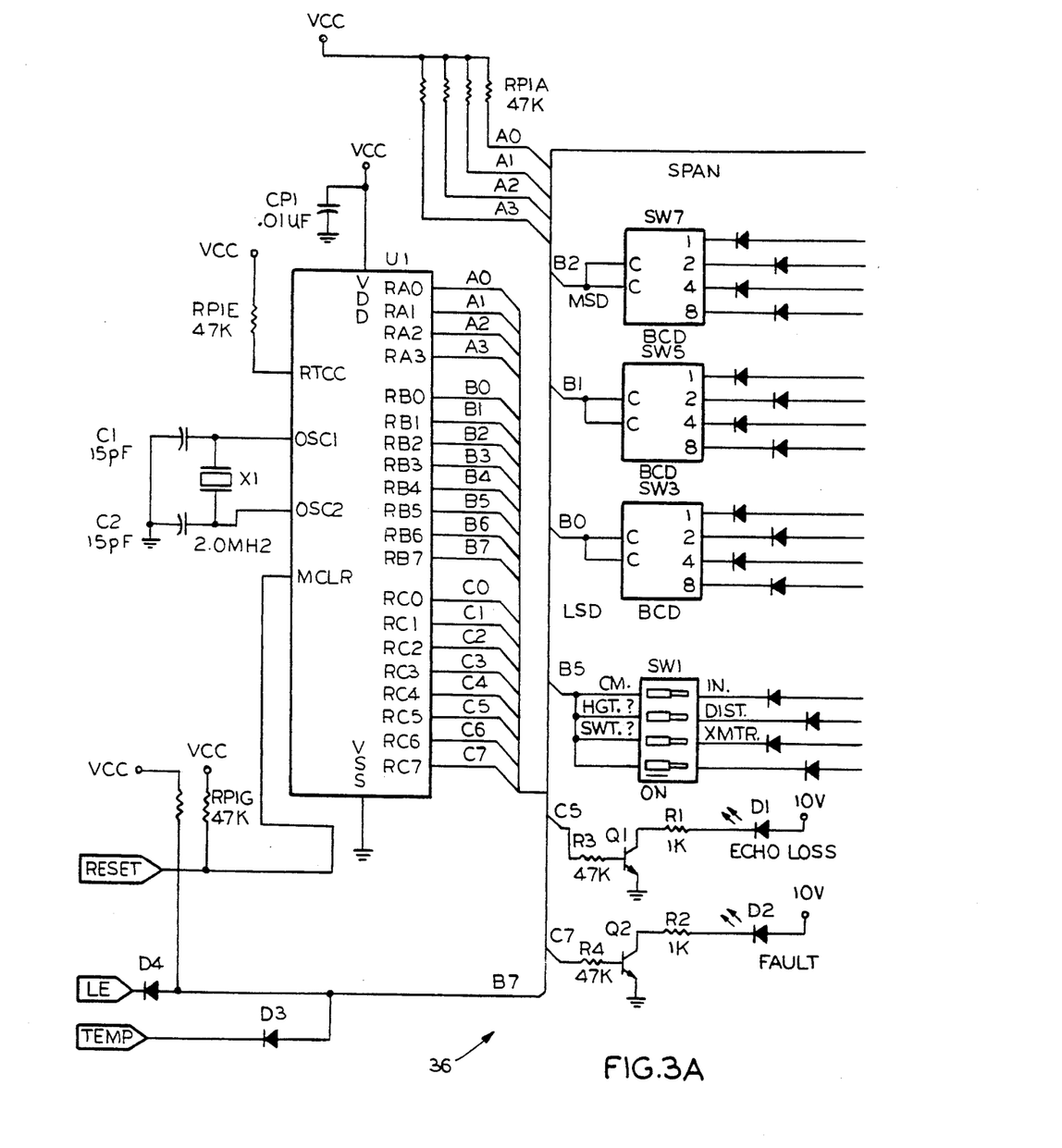
Figure 3B:
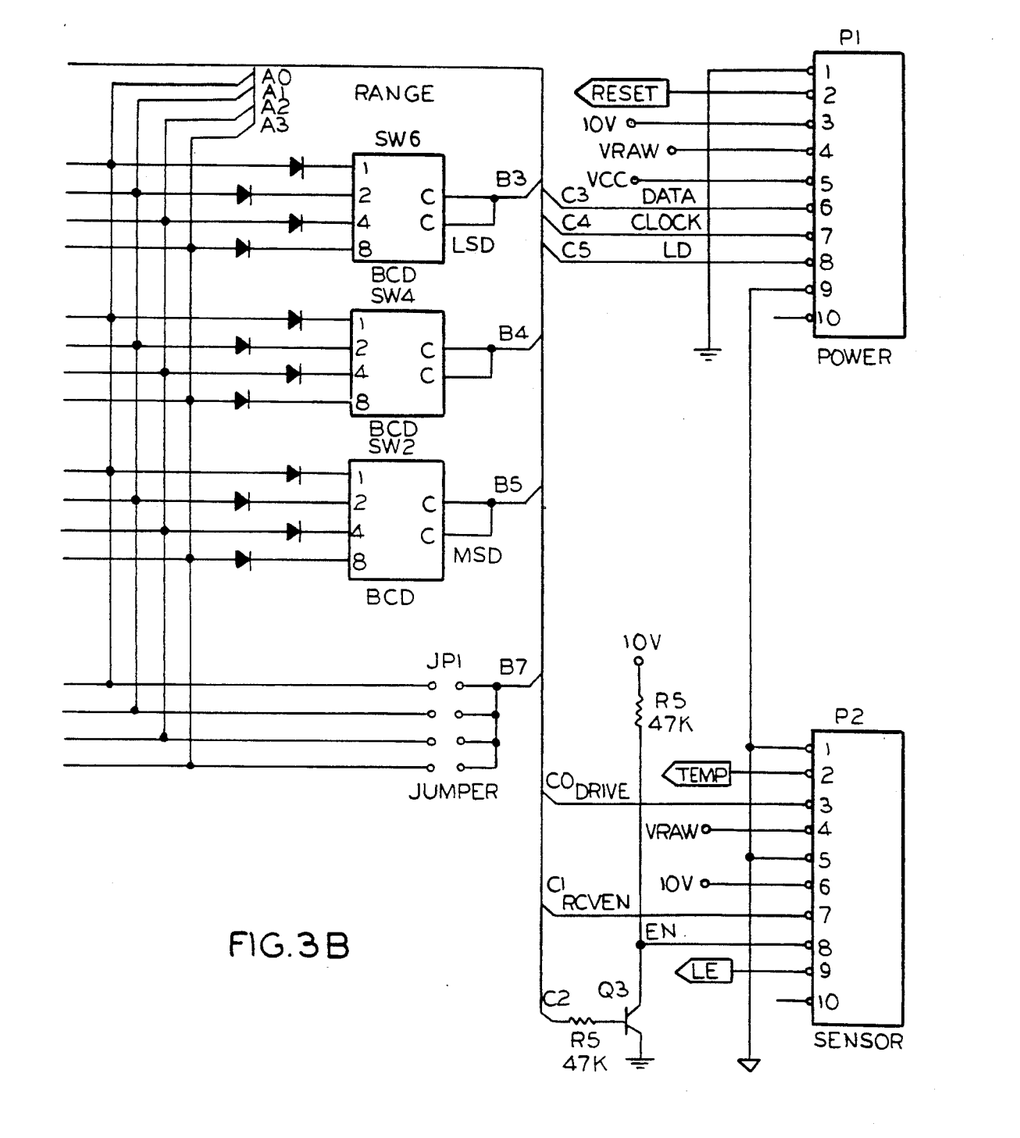

The converter U2 receives input from the logic circuit of FIG. 3 via DATA, CLOCK and *LD control lines connected to the connector J1. Particularly, the logic circuit drives the necessary data into the D/A converter U2 to control the 4 to 20 milliamps current draw of the unit as a whole. The current output of the converter U2 is connected to an amplifier U3B to provide an output voltage.

The current control circuit 44 receives the output voltage from the amplifier U3B at the inverted input of an operational amplifier U1D. The non-inverted input is connected to the wiper of a resistor R8 which is connected in series between the ten volts supply through a resistor R14 and on its opposite side through a resistor R12 to the diodes D6 and D7. The amplifier U1D attempts to maintain its inputs at the same voltage and to do so drives its output higher or lower. The output is connected to a transistor Q2 between the Vraw node and a resistor R15 to ground. A current sense resistor R17 is connected to a junction between the resistor R12 and the diodes D6 and D7 and to ground. All of the current drawn by the unit passes through the current sense resistor R17. Thus, the voltage at the junction of the current sense resistor R17 and diodes D6 and D7 is below the circuit ground by an amount dependent on the current drawn by the unit. Such voltage is divided by the resistors R12, R8 and R14 and the result fed back to the amplifier U1D non-inverted input. The amplifier U1D assures that its input voltages are equal by adjusting its output. If its output increases in voltage, then more current is passed through the transistor Q2 to ground. Thus, the current through the transistor Q2 and the resistor R15 closes the loop and maintains current control as defined by the output of the D/A converter circuit 42 and its output voltage at the amplifier U1D.

With reference to FIG. 3, a schematic diagram illustrates the circuit on the logic printed circuit board 36, see FIG. 1. This circuit includes a connector labelled P1 for connection to the connector J1 of the power supply printed circuit board 34, see FIG. 2. A microprocessor U1 may comprise, for example, a microchip PIC16C57 which is a low power eight-bit controller in a 28-pin one-time programmable PROM package. The microprocessor U1 includes a plurality of I/O ports connected to scan lines A1-A3, B0-B7 and C0-C7. A crystal X1 is connected to the oscillator inputs to provide a two megahertz clock crystal for the microprocessor U1. The *RESET line from the power supply board is pulled up by a resistor RP1G for resetting the microprocessor U1.

A four position dip switch SW1 and six BCD switches SW2-SW7 are provided for customer setup and programming of the microprocessor U1. Particularly, the switches SW1-SW7 are scanned by the microprocessor U1 as by pulling one scan line (B0-B6) low at a time. Each scan line B0-B6 is connected to one of the switches SW1-SW7, as shown. Opposite sides of each switch SW1-SW7 are connected in parallel to scan lines A0-A3. The microprocessor U1 monitors the return signals on the scan lines A0-A3 to detect which switch positions for the scanned switch are closed.

The dip switches on the switch SW1 are provided for selecting use of centimeters and inches, height or distance mode operation, and use as a level switch or range transmitter. The range BCD switches SW2, SW4 and SW6 allow the user to program the maximum distance from the tube end wall 26, see FIG. 1, that is expected. In the illustrated embodiment, range is limited to 24 to 300 inches or 61 to 763 centimeters. The switch SW2 provides the most significant digit, while the switch SW6 provides the least significant digit. The span BCD switches SW3, SW5 and SW7 allow the user to program the span setpoint, i.e. the maximum height that the liquid can be expected to reach. The span is determined from the range setpoint up, as a height in the vessel. Span is limited to between twelve inches and range less twelve inches or thirty centimeters and range less thirty-one centimeters. The range and span switches together with the HGT/DIST switch define the four to twenty milliamp output current operation.

For interface with the amplifier circuit, control lines labelled DRIVE, RCVEN and EN are used. The former two control lines are connected to the microprocessor U1 via scan lines C0 and C1, respectively, while the EN control line is driven from the scan line C2 via a resistor R5 and transistor Q3 for level shifting so that it can be held at zero or ten volts. Return control lines from the amplifier circuit to the logic circuit are labelled *LE and TEMP which are connected to the scan line B7 via diodes D4 and D3. All of the control lines connect to the amplifier circuit via a connector P2 which in turn is connected to the cable 38, see FIG. 1.

The DATA, CLOCK and *LD control lines to the power supply circuit are connected to the respective scan lines C3–C5 C5 from the microprocessor U1. The DATA and CLOCK lines work together to provide serial output of twelve bits of digital data to the D/A converter U2, see FIG. 2. The *LD line pulls low after the complete 12-bit word is shifted out to load the D/A converter's latch circuit.

For local indication, two LED indicators D1 and D2 are included. The LED D1 is an echo loss indicator, while the LED D2 is a fault indicator. The former is controlled by a transistor Q1 from the scan line C6, while the latter is controlled by a transistor Q2 from the scan line C7. Echo loss is used to indicate a loss of system echo which can be caused by a damaged or missing transducer, application problems such as liquid surface foam or agitation or programming errors. The fault indicator is used primarily to show illegal switch settings by the user.

With reference to FIG. 4, a schematic diagram illustrates the circuit on an amplifier circuit board. The amplifier circuit includes a connector J2 for connection via the cable 38 to the logic printed circuit board 36, see FIG. 1.

A drive circuit 50 operates under control of the logic circuit 36 which provides pulses on the DRIVE control line via the connector J2. The logic circuit drives the pulse signal at the 50 kHz frequency of the transducer X1. The DRIVE control line is connected via a resistor R2 to a transistor Q1. The transistor Q1 responds to signals on the DRIVE control line by conducting current from the Vraw node via a resistor R1 through the primary of a transformer T1. The transducer X1 is connected across the secondary of the transformer T1. The approximately square wave drive voltage on the primary side of the transformer T1 is stepped up to approximately 400 volts peak to peak at its secondary for driving the transducer X1.

A capacitor C1 between the resistor R1 and reference comprises a 100 uF capacitor which is charged up through the resistor R1 between cycles of the drive signal to store energy. When the transistor Q1 is turned on the energy stored in the capacitor C1 is used to drive the transducer X1. Thus, the capacitor C1 smooths the current requirements of the transducer drive by storing energy during the off time for use when the transducer X1 is driven.

The transducer X1 comprises a piezoelectric crystal which converts electrical energy to mechanical vibration. This conversion of energy is extremely inefficient, explaining the use of the 400 volt input requirement. In order to prevent damage to other components from such high voltages, a plurality of diodes D1–D6 are connected to the transducer X1 via a resistor R3 and a capacitor C2 to prevent the signals from damaging other components.

The drive circuit 50 is connected to an amplifier circuit 52. A differential video amplifier integrated circuit U1 includes input terminals connected to the drive circuit 50. Particularly, an inverted input is connected to one side of the diode bridge and to Vref, while a non-inverted input is connected to the opposite side of the diode bridge. With the resistor R3 limiting current and the capacitor C2 blocking DC voltages from the drive circuit 50, the diodes D1–D6 assure that the voltage at the non-inverted input is not farther than the forward voltage drop of the diodes from Vref.

The amplifier U1 is a preamplifier which takes the differential input signal and converts it to a differential output to capacitors C8 and C10. An inductor L1 and capacitor C3 provide gain adjustment input and cause the amplifier U1 to act as a band pass circuit centering the band pass on the 50 kHz frequency of the transducer X1. The differential signal from the amplifier U1 is connected through the capacitor C8 and C10 and respective resistors R5 and R6 to inverted and non-inverted inputs, respectively, of an amplifier U2A. The amplifier U2A amplifies the signal and references it to Vref, owing to the connection of the Vref via a parallel capacitor C5 and resistor RPIC to the non-inverted input. The amplifier U2A and associated circuits also perform band pass filtering on the signal. The output of the amplifier U2A is connected via a capacitor C9 and resistor R9 to the inverted input of an additional operational amplifier U2B which provides an additional stage of gain and band pass filtering. The output of the amplifier U2B provides an analog signal representing the signal generated by the transducer X1.

Figure 8:
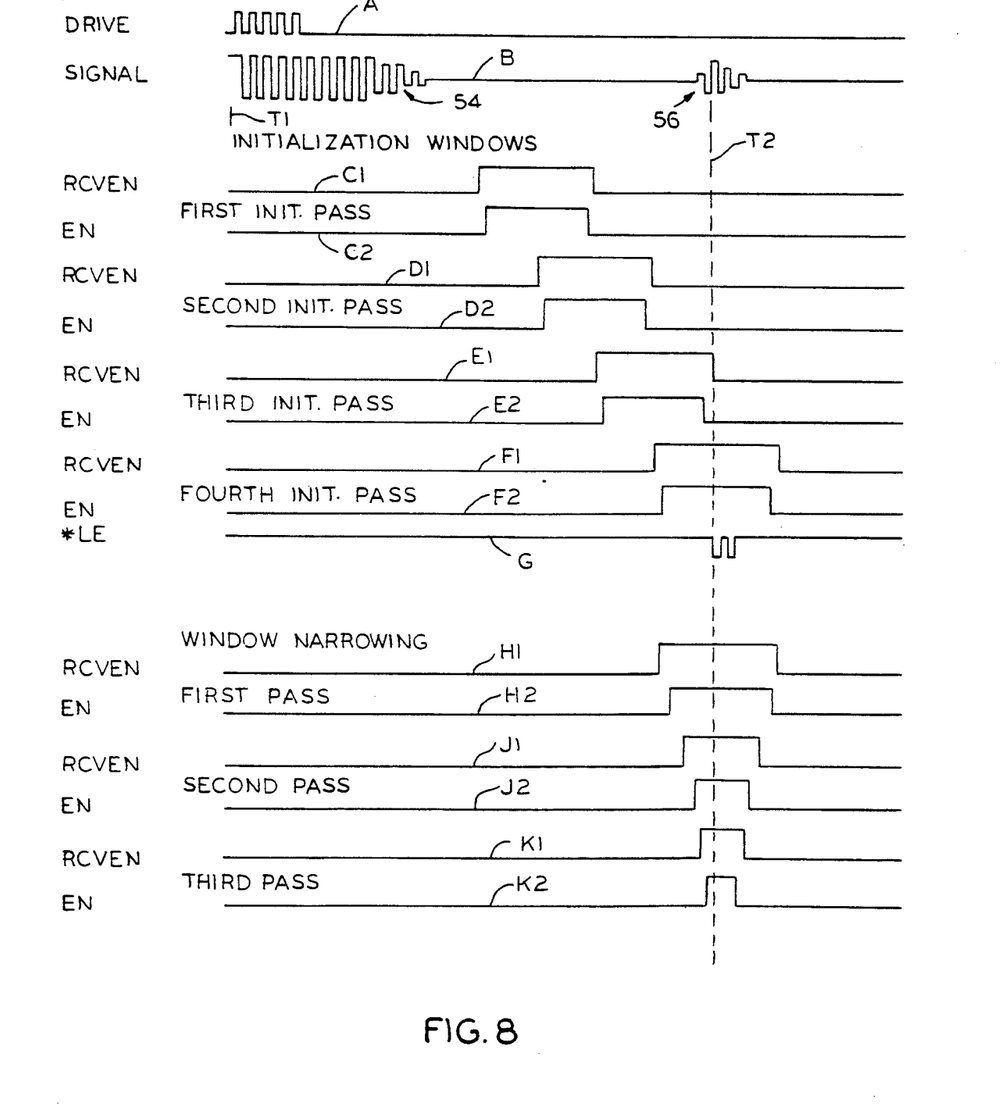
FIG. 8 is a series of curves illustrating operation of the program of FIGS. 5-7.

With reference to FIG. 8, a series of curves illustrate various signals during different stages of operation of the transmitter 10. The curve labelled A illustrates the signal on the DRIVE control line used to drive the transducer X1. The signal on the curve labelled B represents the signal received by the amplifier circuit 52 from the drive circuit 50. Particularly, the transducer X1 when driven provides a sound pulse as output and also continues to ring for a period of time making the transducer X1 incapable of receiving return signals. The ring down time causes a dead band area near the sensor that cannot be used to monitor levels. In the curve labelled B, the ring down is illustrated at 54 which must precede the return or echo signal indicated at 56 in order to distinguish the same.

In order to minimize the dead band, a ring down attenuator circuit 58, see FIG. 4, is provided. The circuit 58 comprises a transistor Q3 having its drain and source connected across the differential output of the amplifier U1 and its gate connected to the junction between a resistor R7 and capacitor C11 between 10 volt supply and Vref. The transistor Q3 acts as a variable resistor to attenuate the signals until the gate voltage charges up and causes the transistor to be a high resistance from drain to source. The values for the resistor R7 and capacitor C11 are selected to assure that the resistance change will attenuate the ring down but still allow normal reception of signals after ring down.

Subsequent to ring down, it is necessary to determine when the return echo signal shown at 56, see FIG. 8, curve B, is received. A comparator circuit 60 is connected to the output of the amplifier circuit second stage operational amplifier U2B. The comparator circuit 60 includes an amplifier U3A having its inverted input connected via resistor R11 to the output of the operational amplifier U2B. Vref is connected via a diode D8 and resistor RP1D to the non-inverted input to establish the threshold for the comparator circuit 60. Thus, when the received signal exceeds the threshold at the non-inverted input, then the output, representing the signal on the line *LE is pulled low.

A series connected diode D11 and resistor R14 between the non-inverted input and the output are provided to make the amplifier U3A act as a latch. Thus, the first low transition of the output causes the threshold at the non-inverted input to be shifted such that the output stays low until the signal on the EN control line connected via the diode D7 to the inverted input is pulled low to reset the latch. As discussed below, the *LE control line is used by the logic circuit to determine the time of reception of the sound signal representing the time difference between the initiation of the drive signal at a first time T1, see FIG. 8, curve A, and the receipt of the return echo signal exceeding the threshold at a time T2, see curve B. Thus, the logic circuit has control of the transmission of the sound signal and also receives an indication of the time of reception of the reflected signals to determine the time of flight and thus compute the actual distance to the liquid surface.

The control line EN from the logic circle acts as an enable control allowing the logic circuit to enable the reception of signals when it is high. This is used to set a receive window for receiving the *LE signal to prevent spurious signals from creating instable operation such as by ignoring agitator blades, smoothing severe liquid surface agitation and ignoring conducted and radiated electromagnetic interference. This EN control line is also controlled by the logic circuit to allow the amplifier circuit 52 to stabilize prior to enabling reception.

A significant portion of the power used by the transmitter 10 is in the amplifier circuit 52. Since the transmitter 10 is of the two-wire type, minimal power is available under certain situations, such as when the current is relatively low, i.e. close to four milliamps DC. In order to minimize consumption of power, the transmitter 10 is configured to normally operate in a sleep mode as by disabling the amplifier circuit 52 when it is not necessary for operation and awakening the amplifier circuit 52 when necessary. In order to further minimize power consumption, the "window" of time during which the amplifier circuit is energized is kept to a minimum and centered about an expected receive time for a return echo. This window is controlled by the RCVEN control line from the logic circuit via the connector J2.

The RCVEN control line is connected via a resistor R5 to the gate of a transistor Q2. The source is connected via a capacitor C4 to Vraw, while the drain is connected to a resistor R13 to provide a control signal for powering the amplifiers U1 and U2A of the amplifier circuit 52. The RCVEN control line causes the transistor Q2 to conduct and thus pulls current from the amplifiers U1 and U2A and a resistor RP3C to a voltage reference circuit 62. The current is dumped into the capacitor C4 to smooth the current draw of the amplifier circuit 52 by storing current drawn while Q2 is on until it turns off. After Q2 turns off, the energy in the capacitor C4 is discharged through a resistor R16 to prepare for the next cycle.

The operation of the transistor Q2 permits the amplifier circuit 52 to be turned on only when needed and thus to draw the minimum amount of power supply current possible. This feature allows the transmitter to operate on only four milliamps DC.

The voltage reference circuit 62 includes an amplifier U4A having a non-inverted input connected to the resistor RP3C and another resistor RP3D connected to ten volt supply. The amplifier U4A establishes a reference voltage used throughout the amplifier circuit 52. This voltage is not DC, but rather floats up to near ten volts when the transistor Q2 is off. When the transistor Q2 is on, the reference Vref is held near five volts. Diodes D9 and D10 are included to assure that the Vref voltage is never lower than a diode drop below ground nor higher than a diode drop above ten volts.

The velocity of sound through air is dependent on the temperature of the air. The warmer the air the faster sound travels. In order to obtain an accurate measurement of the distance that sound waves from and to the transducer X1 travel it is necessary to know to the air temperature. The transmitter 10 obtains a temperature indication using a temperature ramp circuit 64, see FIG. 4.

The ten volt supply is connected via a temperature dependent current source Q4 to the non-inverted input of an amplifier U4B and to a temperature stable capacitor C12. The source Q4 provides current to charge the capacitor C12. The logic circuit via the RCVEN control line is connected via a resistor R8 to a transistor Q5 connected across the non-inverted input of the amplifier U4B. The logic circuit triggers the transistor Q5 to reset the capacitor C12 and when the logic circuit pulls the RCVEN control line low the ramp is allowed to start up. As the capacitor C12 charges up, the output of the amplifier U4B ramps up at a slope dependent on the temperature of the transducer X1 as sensed by the source Q4. The output of the amplifier U4B is connected to the inverted input of a comparator U3B. When this output reaches the threshold of the comparator U3B set at its non-inverted input, then the output of the comparator U3B is pulled low. The TEMP control line is returned to the logic circuit as illustrated above in FIG. 3. Thus, the logic circuit uses RCVEN control line to switch the transistor Q5 to reset the capacitor C12 and then monitors the TEMP control line to determine the time that the ramp requires to reach the threshold. This time is a function of the temperature of the transducer X1 and is used by the logic circuit to compensate for the velocity of sound.

The portion of the circuit on the amplifier board surrounded by the dotted line is encapsulated with a potting compound. This includes the transducer X1 and the capacitors C1 and C4. The use of encapsulation along with current limiting resistors ensures that any failure does not cause a spark, thus assuring intrinsic safety.

The microprocessor U1 includes a program stored in its internal PROM so that it is used as a sequence counter. The counter steps through a program illustrated in the flow diagrams of FIGS. 5–7 for sensing level and outputting a signal representative thereof at the terminal block TB1.

Figure 5:
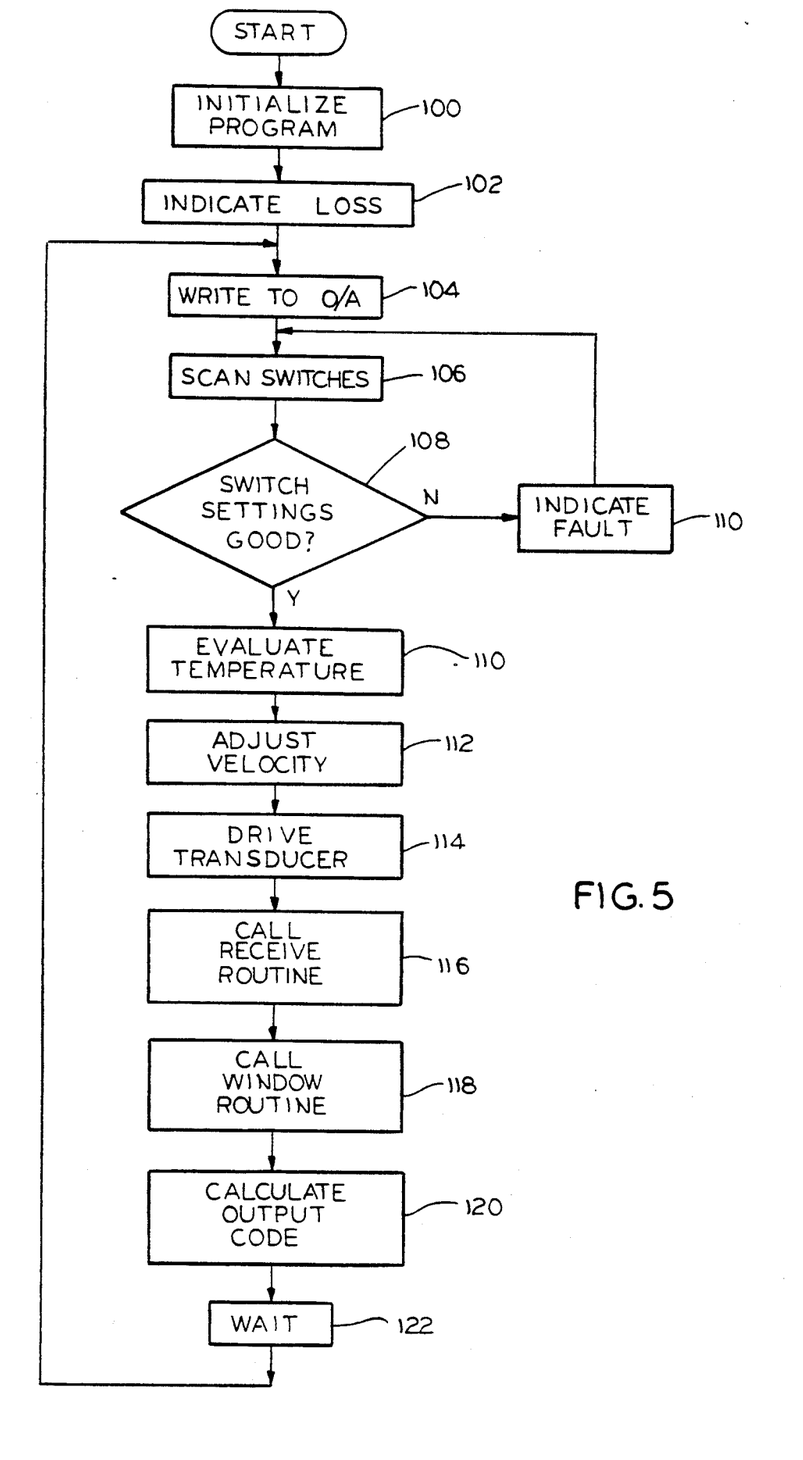
FIG. 5 is a flow diagram illustrating a main control program implemented by the microprocessor of FIG. 3.

With reference to FIG. 5, a flow diagram illustrates operation of the software for a main control program. After startup, the program begins at a block 100 which initializes the program comprising the power on and start routine, as is conventional. The control then advances to a block 102 which indicates a loss of echo as by illuminating the LED D1, see FIG. 3. An output code is set corresponding to a current greater than twenty-two milliamps. The output code is written to the D/A converter U2, FIG. 2, at a block 104. As a result, a current of greater than twenty-two milliamps is drawn from the loop to indicate loss of echo during startup and initialization functions.

At a block 106 the switches on the logic board 36 are scanned, as discussed above, to determine their settings. A decision block 108 determines if the switch settings are acceptable, i.e. whether or not they are acceptable values for span and range. If not, then a fault is indicated at a block 110 which illuminates the LED D2, see FIG. 3, and control returns to the block 106 until acceptable settings are obtained.

Once acceptable settings are obtained, then the transducer temperature is evaluated at a block 110. This comprises operating the temperature ramp circuit 64 of FIG. 4 to determine temperature. The determined temperature is used at a block 112 for determining the suitable velocity adjustment necessary according to sensed temperature. This adjustment may be in the form of an equation relating velocity to temperature or a lookup table which provides a suitable velocity correction according to sensed temperature.

The transducer X1 is driven at a block 114. Particularly, and with reference to the curve A of FIG. 8, the transducer X1 is driven at 50 kHz for a preselected number of pulses on the order of, for example, five pulses beginning at the time T1. Simultaneously, an internal counter used for counting a time duration from the initialization of the drive signal until a return echo is received is reset to zero. Thereafter, a receive routine is initiated at a block 116 which is used to determine the time of flight between transmission of a drive signal and return of a reflected signal. A window routine is then called at a block 118 to adjust size of the window during which the receive routine is operable to energize the amplifier circuit 52 of FIG. 4 and also enable the comparator circuit 60. Finally, the output code for the sensed level, adjusted for temperature, is calculated at a block 120 comprising the digital signal to be written to the D/A converter U2, see FIG. 2. The output code is calculated based on the switch settings for range and span as well as the recorded time of flight, as is conventional Control then waits at a block 122 prior to returning to the block 104. This wait is provided to assure low on time duty cycle which in effect limits the number of cycles permissible to further minimize power consumption.

Figure 6:
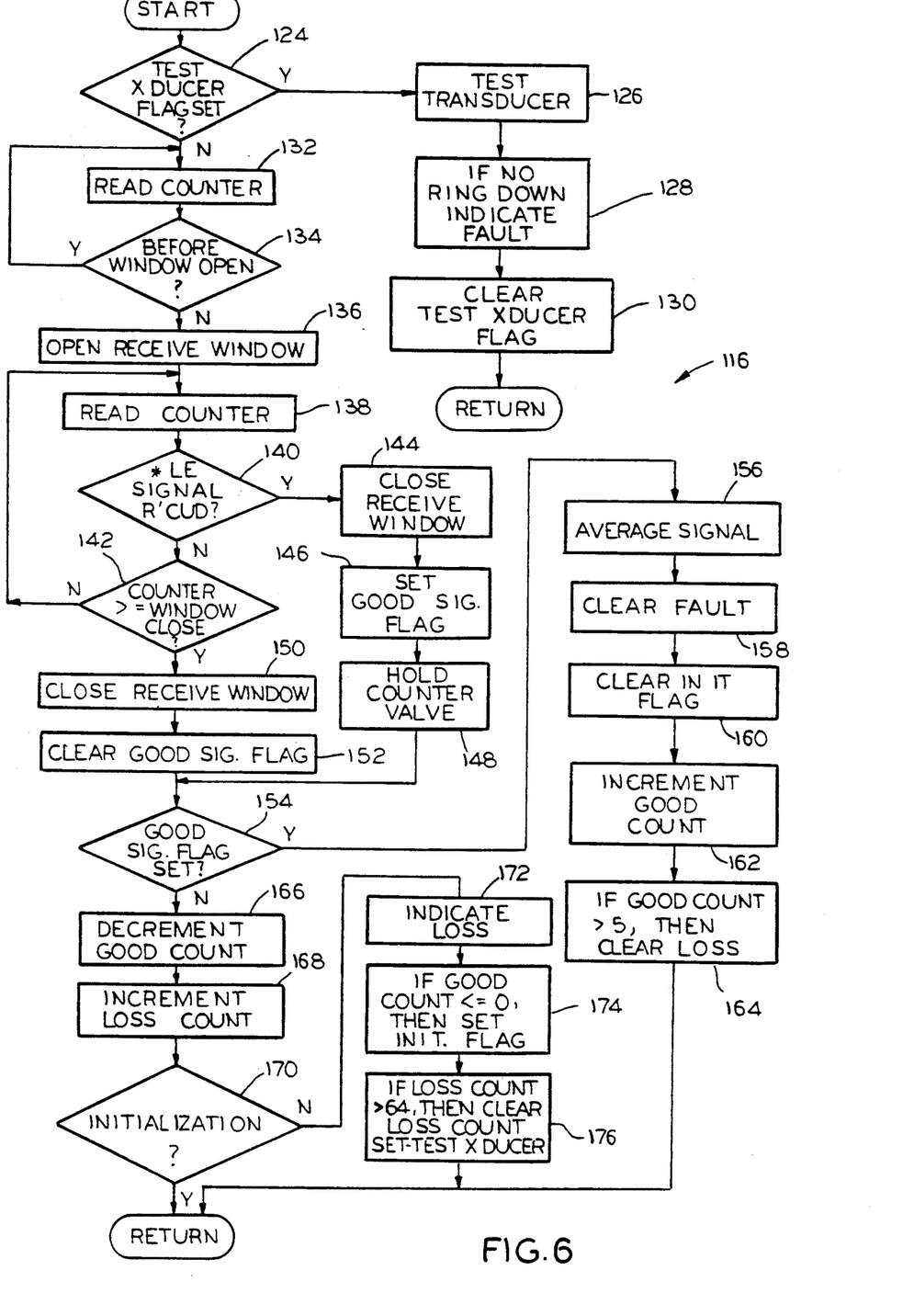
FIG. 6 is a flow diagram illustrating a receive routine utilized by the main program of FIG. 5.

With reference to FIG. 6, a flow diagram illustrates the receive routine 116.

The receive routine begins at a decision block 124 which determines if a test transducer flag is set. This flag is set, as discussed below, when a loss of echo condition is maintained for a plurality of cycles of operation. If the flag is set, then the transducer is tested at a block 126 which drives the same and looks for a ring down of the transducer X1 to define the dead band. This condition is illustrated in curve B of FIG. 8, particularly the portion labelled with the numeral 54. If no ring down occurs, then a fault condition is indicated at a block 128. Thereafter, the clear transducer flag is cleared at a block 130 and the receive routine ends and control returns to the main program.

If the test transducer flag is not set, as determined at the decision block 124, then the counter is read at a block 132. This is the counter that is cleared at the initiation of the drive signal. A decision block 134 determines if the counter value represents a time before the time at which the window is to open. If so, then control loops back to the block 132 until a sufficient time has passed that the window is to open. Once this occurs, then the receive window is opened at a block 136. The receive window is opened by pulling the RCVEN control line to the amplifier circuit board high and then waiting a sufficient time to allow stabilization of the amplifier circuit 52 and then pulling the EN control line high which is level shifted with the transistor Q3 and resistor R5, see FIG. 3, to enable the comparator circuit 60, see FIG. 4.

The counter is again read at a block 138 and a decision block 140 determines if the *LE control line from the comparator circuit is pulled low, indicating the receipt of a return echo pulse. If not, then a decision block 142 determines if the counter value is greater than or equal to the window close time and if not loops back to the block 138.

If the *LE signal is pulled low, as determined at the block 140, then the receive window is closed at a block 144. The operation for closing the receive window is opposite that for opening the same. Particularly, the EN control line is set low to disable the comparator circuit 60, see FIG. 4, and then after a predetermined wait period, the RCVEN control line is set low. As a result, the logic circuit looks for an echo only until one is received and then turns the power off to the amplifier circuit 52. Thereafter, a GOOD SIG flag is set at a block 146 indicating the receipt of a return pulse and the counter value is held at a block 148.

Returning to the decision block 142, if the counter value is greater than or equal to the window close time before the *LE control line is pulled low, then the receive window is closed at a block 150. This block is similar in function to the block 144 discussed above but is operable to close the window without the receipt of a return pulse. Typically, such a situation occurs of the window is too narrow to allow the receipt of a reflective pulse after a significant level change. Subsequently, the GOOD SIG flag is cleared at a block 152 to indicate the fact the return echo pulse is not received.

From either block 148 or 152 a decision block 154 determines if the GOOD SIG flag is set. If so, then an average signal routine is implemented at a block 156. Particularly, this block maintains a running average of the counter value for a select number, such as, for example, eight cycles to offset the effects of wave motions and the like in the liquid. Since a good signal was received there is no fault condition and the same is cleared at a block 158 and an INIT flag is cleared at a block 160. Use of the INIT flag is discussed more specifically below. Thereafter, a GOOD COUNT register is incremented at a block 162 to indicate the number of occurrences of a good reading, and at a block 164 if the GOOD COUNT register is greater than five, than any echo loss condition is cleared at a block 164 and the routine ends.

Returning to the decision block 154, if the GOOD SIG flag is not set, then the GOOD COUNT register is decremented at a block 166 and a LOSS COUNT register is incremented at a block 168. The LOSS COUNT register represents the number of cycles in which no return echo is received. A decision block 170 then determines if control is in an initialization cycle. If so, then the routine ends. If not, then control advances to a block 172 which indicates a loss as by illuminating the echo loss LED D1, see FIG. 3. A block 174 then determines if the GOOD COUNT register value is less than or equal to zero and if so sets an INIT flag so that an initialization routine can be performed. A block 176 then determines if the LOSS COUNT register value is greater than 64 and if so clears the same and sets the test transducer flag so that during the next cycle of operation the transducer can be tested as discussed above relative to blocks 126–130. The routine then ends.

Figure 7:
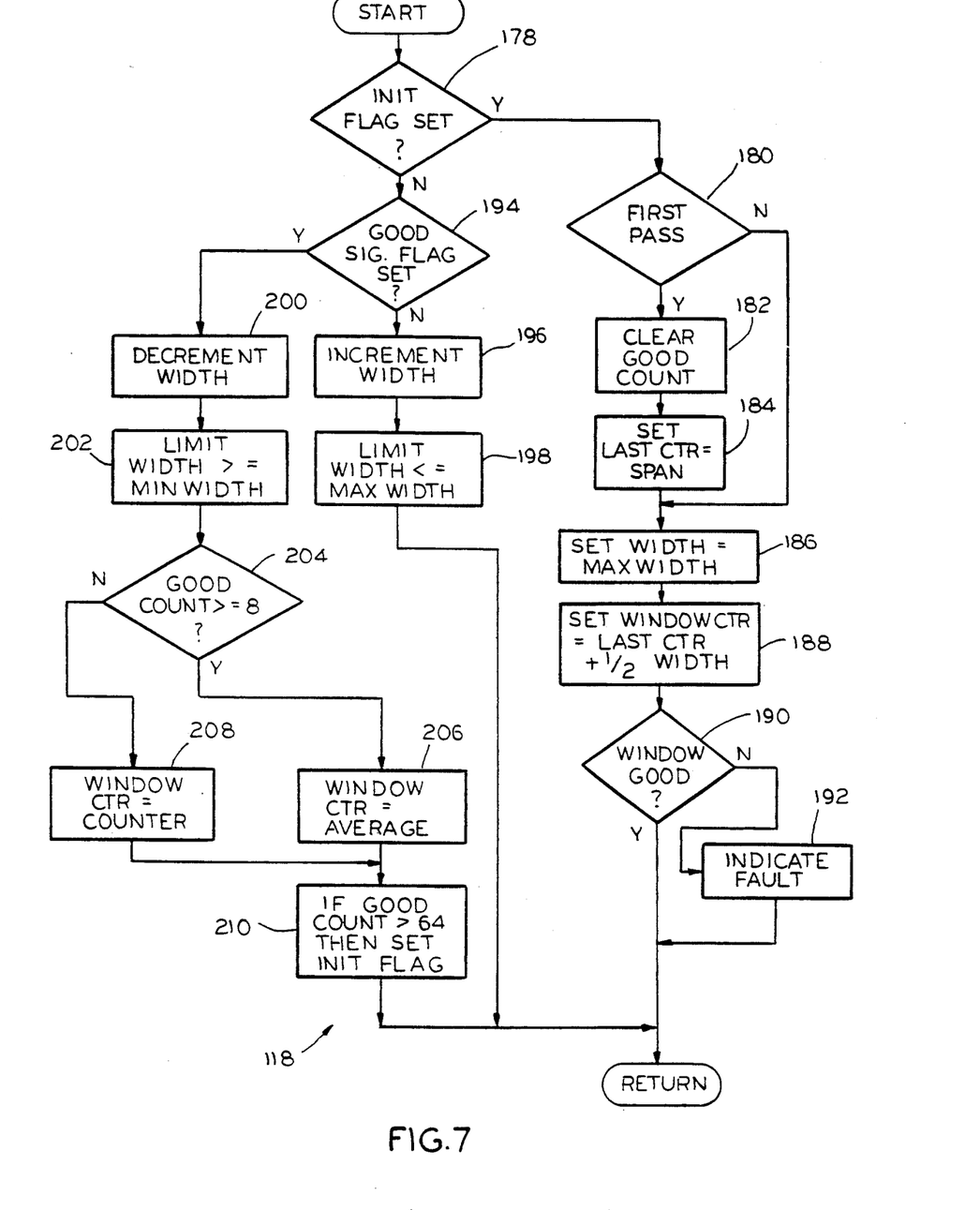
FIG. 7 is a flow diagram illustrating operation of a window routine implemented by the main program of FIG. 5.

With reference to FIG. 7, a flow diagram illustrates the operation of the software for the window routine 118.

The window routine 118 begins at a decision block which determines if the INIT flag has been set. This can be set at power-up or at the block 174, see FIG. 6. If so, then a decision block 180 determines if it is the first pass through the initialization routine. If so, then the GOOD COUNT register is cleared at a block 182 and a value LAST CTR, representing the last centerpoint for the window, is set equal to the user selected span value at a block 184. Thereafter, or if not the first pass, as determined at the decision block 180, then the value WIDTH is set equal to the maximum permissible width at a block 186 and the WINDOW CTR is set equal to the LAST CTR plus one-half of the width at a block 188. The maximum width value is an arbitrary selected value. The block 188 sets the WINDOW CTR so that it opens at the beginning of the span and closes at the maximum width value from the span. A decision block 190 then determines if the window settings are acceptable, meaning that they are not too soon or late according to the range and span settings. If not, then a fault is indicated at a block 192. Otherwise, the call window routine ends and control returns to the main program.

The effect of the initialization routine is illustrated in the series of curves under the heading "Initialization Windows" in FIG. 8. The first pass through the routine is illustrated showing the operation of the RCVEN and EN control lines as represented by the curves C1 and C2, respectively. The RCVEN control line is pulsed for the maximum window width and starting at the time corresponding to the span value. The EN control line is pulsed for a slightly shorter time duration entirely within the window of the RCVEN pulse, as discussed above relative to the flow diagram of FIG. 6. As the initialization routines advances to each successive cycle, the window is shifted in time by a factor corresponding to one-half of the WIDTH value due to the equation implemented at the block 188. Particularly, the second initiation pass is illustrated by the curves D1 and D2, the third initialization pass is illustrated by the curves E1 and E2, and the fourth initialization pass is illustrated by the curves F1 and F2.

In the illustrated initialization example, the *LE control line is pulled low, indicating receipt of a return echo, while the window is open during the fourth initialization pass. This occurrence is sensed at the decision block 140, see FIG. 6, resulting in the GOOD SIG flag being set at the block 146 and the INIT flag being cleared subsequently at the block 160 to terminate the initialization routine. Thereafter, control would operate to implement normal level sensing.

Returning to the window routine 118, and specifically the decision block 178, once the INIT flag is cleared, then control advances to a decision block 194 which determines if the GOOD SIG flag is set. The routine is operable to minimize the size of the window in order to minimize power requirements of the amplifier circuits 52, see FIG. 4. This is done by continually decreasing the size of the window as long as good signals are received and conversely increasing the size of the window if no return echo is received. As such, if the GOOD SIG flag is not set then the width is incremented at a block 196 by a predetermined amount and a block 198 limits the width to ensure that it is less than or equal to the preselected MAXWIDTH. The routine then ends. If the GOOD SIG flag is set, as determined at the decision block 194, then the width is decremented at a block 200 and a block 202 limits the width so that it is greater than or equal to a MINWIDTH representing a minimum desired width. The minimum width may correspond to plus or minus two inches, while the maximum width might correspond to two to three feet.

A decision block 204 then determines whether or not the GOOD COUNT register value is greater than or equal to eight, indicating that full averaging function for eight successive signals has been obtained. If so, then the WINDOW CTR is set equal to the average at a block 206. If not, then the WINDOW CTR is set equal to the counter value at a block 208. Thus, the average value is used only after sufficient readings have been obtained to render it reliable. A block 210 then determines if the GOOD COUNT register value is greater than sixty-four and if so sets the INIT flag so that initialization routine is performed. This provides for periodic initialization of the window setting after sixty-four cycles with a GOOD COUNT reading which, assuming approximately one second per cycle, occurs once every sixty-four seconds. The call window routine then ends and control routines to the main program of FIG. 5.

The window narrowing achieved by operation of the block 200 is illustrated by the curves under the heading "Window Narrowing" of FIG. 8. Particularly, during the first pass subsequent to initialization, the window of the RCVEN signal represented by the curve H1 corresponds to the curve F1, discussed above. During the second pass, the window is narrowed by the preselected decrement amount, as illustrated by the curve J1. Finally, during the third pass, the window is narrowed to that illustrated by the curve K1. Assuming the *LE control line of curve G represents the sensed level, then the window represented by the curve K1 would likely remain until a significant shift in level occurs so that a good signal is no longer received. Such a narrow window might also likely represent the minimum width usable as it must be sufficient to capture the return echo signal.

Thus, there is disclosed herein an ultrasonic through air transmitter which is normally operable in a sleep mode by disabling power to an amplifier circuit and disabling a comparator circuit to conserve power and energize such circuits only as necessary to sense a return echo signal. Further, the duty cycle of the operation of the amplification circuit is continually optimized to further minimize power consumption.

Further, the transmitter 10 is designed to be intrinsically safe and suitable for hazardous locations using an explosion-proof housing and a circuit with limited energy storage to prevent spark occurrence.

The circuit uses duty cycle modulation and limits duty cycle during operating periods to reduce power requirements.

Further, the instrument compensates for temperature changes.

We claim:

1. An instrument for sensing level of a material comprising:
   a transducer and means for mounting said transducer in proximity to a material, the level of which is being sensed;
   a drive circuit connected to said transducer and including means for periodically energizing said transducer to transmit an energy pulse to be reflected off of a surface of the sensed material;
   an amplifier circuit connected to said transducer and including amplifier means for developing an analog signal having a magnitude corresponding to reflected energy received by said transducer;
   a detector circuit connected to said amplifier circuit for determining if said analog signal has a level above a select threshold, representing receipt of a return echo pulse; and
   a control circuit operatively coupled to said drive circuit, said amplifier circuit and said detector circuit and including level determining means for determining a time difference between a first time when said drive circuit energizes said transducer and a second time when said analog signal is above said threshold, said time difference representing level, and amplifier control means for energizing said amplifier circuit for a select minimum time duration commencing subsequent to energization of said transducer and terminating after receipt of a return echo pulse.

2. The instrument of claim 1 wherein said control circuit further comprises detector control means for enabling said detector circuit for a select minimum time duration commencing subsequent to energization of said transducer and terminating after receipt of a return echo pulse.

3. The instrument of claim 2 wherein said detector control means enables said detector circuit subsequent to said amplifier control means energizing said amplifier circuit.

4. The instrument of claim 1 wherein said amplifier circuit comprises a power source connected to a switch controlled by said amplifier control means for selectively controlling coupling of said power source to said amplifier means.

5. The instrument of claim 1 wherein said amplifier circuit comprises a ring down attenuator circuit operatively coupled to said transducer.

6. The instrument of claim 1 wherein said control circuit includes window determining means for selecting said time duration to be a minimum necessary to allow receipt of a return echo pulse.

7. The instrument of claim 6 wherein said window determining means selects a start time for said time duration relative to a previously determined time difference.

8. A two wire ultrasonic transmitter for sensing level of a material and controlling current of power supplied thereto to a magnitude representing sensed level, comprising:
   a transducer;
   means for mounting said transducer in proximity to a material, the level of which is being sensed;
   a power supply circuit for receiving power for operating said transmitter;
   a drive circuit connected to said transducer and said power supply circuit and including means for periodically energizing said transducer to transmit an energy pulse to be reflected off of a surface of the sensed material;
   an amplifier circuit connected to said transducer and including amplifier means for developing an analog signal having a magnitude corresponding to reflected energy received by said transducer;
   a control circuit operatively coupled to said drive circuit and said amplifier circuit and including level determining means for determining a time difference between a first time when said drive circuit energizes said transducer and a second time when said analog signal is above a select threshold, said time difference representing level, and amplifier control means for energizing said amplifier circuit for a select minimum time duration commencing subsequent to energization of said transducer and terminating after receipt of a return echo pulse; and
   current control means coupled to said level determining means for controlling current received by said power supply circuit to a magnitude representing sensed level.

9. The transmitter of claim 8 wherein said control circuit further comprises a detector circuit connected to said amplifier circuit for determining if said analog signal has a level above said select threshold, representing receipt of a return echo pulse and detector control means for enabling said detector circuit for a select minimum time duration commencing subsequent to energization of said transducer and terminating after receipt of a return echo pulse.

10. The transmitter of claim 9 wherein said detector control means enables said detector circuit subsequent to said amplifier control means energizing said amplifier circuit.

11. The transmitter of claim 8 wherein said amplifier circuit comprises a switch controlled by said amplifier control means for selectively controlling coupling of said power supply circuit to said amplifier means.

12. The transmitter of claim 8 wherein said amplifier circuit comprises a ring down attenuator circuit operatively coupled to said transducer.

13. The transmitter of claim 8 wherein said control circuit includes window determining means for periodically decreasing said time duration upon receipt of a return echo pulse.

14. The transmitter of claim 13 wherein said window determining means includes means for increasing said time duration in response to failure to receive a return echo pulse prior to termination of said time duration.

15. The transmitter of claim 13 wherein said window determining means selects a start time for said time duration relative to a previously determined time difference.

16. The transmitter of claim 8 wherein said current control means controls said current to a range of 4–20 mA dc.

17. The transmitter of claim 8 wherein said control circuit further comprises a drive control circuit for operating said drive circuit to transmit a plurality of energy pulses seriatim commencing at said first time.

18. The transmitter of claim 8 further comprising means for sensing temperature at said transmitter and wherein said level determining means includes means for compensating sensed level responsive to sensed temperature.

19. An ultrasonic transmitter for sensing level of a material and including a transducer self-test mode of operation, comprising:

a transducer;

means for mounting said transducer in proximity to a material, the level of which is being sensed;

a drive circuit connected to said transducer and including means for periodically energizing said transducer to transmit a sound energy pulse to be reflected off of a surface of the sensed material;

a receive circuit connected to said transducer for developing a signal having a magnitude corresponding to reflected sound energy received by the transducer; and a control circuit operatively controlling said drive circuit and said receive circuit, each said drive circuit and receive circuit normally being disabled by said control circuit, said control circuit including a self-test mode of operation means for periodically enabling the drive circuit for a select time duration to transmit sound energy pulses to be reflected off of a surface of the sensed material and for subsequently enabling the receive circuit and monitoring means for determining if the transducer continues to transmit sound energy pulses subsequent to said select time duration to insure proper operation of the transducer.

20. The receive circuit of claim 19 wherein said control circuit further comprises means for commencing operation of said self-test mode operation means in response to absence of a return echo pulse received by said receive circuit.

* * * * *